(12) United States Patent
Tanno et al.

(10) Patent No.: US 11,426,139 B2
(45) Date of Patent: Aug. 30, 2022

(54) RADIOGRAPHIC IMAGING APPARATUS

(71) Applicant: Shimadzu Corporation, Kyoto (JP)

(72) Inventors: Keiichi Tanno, Kyoto (JP); David Thibault Pelletier, Laval (CA)

(73) Assignee: Shimadzu Corporation, Kyoto (JP)

( * ) Notice: Subject to any disclaimer, the term of this patent is extended or adjusted under 35 U.S.C. 154(b) by 285 days.

(21) Appl. No.: 16/698,594

(22) Filed: Nov. 27, 2019

(65) Prior Publication Data

US 2020/0289079 A1    Sep. 17, 2020

(30) Foreign Application Priority Data

Mar. 13, 2019    (JP) .............................. JP2019-046272

(51) Int. Cl.
| | | |
|---|---|---|
| *A61B 6/00* | (2006.01) | |
| *G06T 5/00* | (2006.01) | |
| *G06T 5/50* | (2006.01) | |
| *G01N 23/04* | (2018.01) | |
| *A61B 6/04* | (2006.01) | |

(52) U.S. Cl.
CPC ............ *A61B 6/547* (2013.01); *A61B 6/0407* (2013.01); *A61B 6/481* (2013.01); *A61B 6/5241* (2013.01); *G01N 23/04* (2013.01); *G06T 5/002* (2013.01); *G06T 5/50* (2013.01); *G06T 2207/10116* (2013.01); *G06T 2207/20216* (2013.01); *G06T 2207/20224* (2013.01)

(58) Field of Classification Search
CPC .............................. A61B 6/481; A61B 6/5241
See application file for complete search history.

(56) References Cited

U.S. PATENT DOCUMENTS

| | | | | |
|---|---|---|---|---|
| 2011/0206183 A1* | 8/2011 | Tanaka | .................. | A61B 6/481 |
| | | | | 378/62 |
| 2017/0091908 A1 | 3/2017 | Takeda et al. | | |

FOREIGN PATENT DOCUMENTS

| | | |
|---|---|---|
| JP | H03-251233 A | 11/1991 |
| JP | 2011-172644 A | 9/2011 |
| WO | 2015/178350 A | 11/2015 |

OTHER PUBLICATIONS

Notice of Reasons for Refusal, dated May 31, 2022, issued from the Japanese Patent Office in connection with counterpart Japanese Patent Application No. 2019-046272, with English-language machine translation of the same (8 pages).

\* cited by examiner

*Primary Examiner* — Dani Fox
(74) *Attorney, Agent, or Firm* — Muir Patent Law, PLLC

(57) ABSTRACT

A radiographic imaging apparatus includes an image generator configured to generate a plurality of first images and a plurality of second images, and an image processor configured to align common regions between the plurality of first images and generate a difference long image by splicing images obtained by subtracting a plurality of corrected images from the plurality of second images.

8 Claims, 7 Drawing Sheets

GENERATION OF
SMOOTHED MOVEMENT VECTOR

RADIOGRAPHIC IMAGING APPARATUS

CROSS-REFERENCE TO RELATED APPLICATIONS

This application claims the benefit of priority to Japanese Patent Application No. 2019-046272 filed on Mar. 13, 2019. The entire contents of this application are hereby incorporated herein by reference.

BACKGROUND OF THE INVENTION

Field of the Invention

The present invention relates to a radiographic imaging apparatus, and more particularly, it relates to an X-ray imaging apparatus configured to generate a long image.

Description of the Background Art

Conventionally, an X-ray diagnostic imaging apparatus configured to irradiate a subject with X-rays and generate a long image is known. Such an X-ray diagnostic imaging apparatus is disclosed in Japanese Patent Laid-Open No. 2011-172644, for example.

An X-ray diagnostic imaging apparatus disclosed in Japanese Patent Laid-Open No. 2011-172644 includes a table, an imager, a controller, and an image processor. The controller is configured or programmed to perform control of imaging a subject at a plurality of stages while stepping at least one of the imager or the table in the body axis direction of the subject. The image processor is configured to process image data obtained by imaging at the plurality of stages to generate long image data.

Japanese Patent Laid-Open No. 2011-172644 discloses that when a range to be imaged is wide as in the case in which a blood vessel of the lower limb is imaged, imaging is performed several times, and a long image is generated. Japanese Patent Laid-Open No. 2011-172644 discloses that a subtraction image in which a contrast portion is highlighted is obtained by subtracting mask image data before a contrast agent is injected from contrast image data after the contrast agent is injected.

Although not disclosed in the Japanese Patent Laid-Open No. 2011-172644, noise may be generated randomly in an X-ray image. The X-ray image in which noise has been generated is used such that the quality of the subtraction image may deteriorate.

Although not disclosed in Japanese Patent Laid-Open No. 2011-172644, when a difference image (subtraction image) is generated using a normal X-ray image, a correction may be made to reduce noise using an X-ray image obtained by imaging the subject a plurality of times. However, a difference long image is generated by splicing a plurality of X-ray images captured by changing an imaging position, and thus the amount of radiation exposure to the subject is larger than that at the time of normal X-ray imaging. Therefore, when X-ray image capturing for generating a difference long image and X-ray image capturing for correction are separately performed for correction to reduce noise, the number of times of long image capturing increases, and the amount of radiation exposure disadvantageously increases.

SUMMARY OF THE INVENTION

The present invention is intended to solve the above problem. The present invention aims to provide a radiographic imaging apparatus capable of significantly reducing or preventing a decrease in the quality of a difference long image while significantly reducing or preventing an increase in the amount of radiation exposure to a subject.

In order to attain the aforementioned object, a radiographic imaging apparatus according to an aspect of the present invention includes a table on which a subject is placed, an imager configured to irradiate the subject placed on the table with radiation and detect the radiation transmitted through the subject to image the subject, a moving mechanism configured to change a relative position between the table and the imager, an image generator configured to generate a plurality of first images obtained by imaging the subject in such a manner as to include common regions between the plurality of first images while the relative position between the table and the imager is changed by the moving mechanism, and a plurality of second images obtained by imaging the subject while the relative position between the table and the imager is changed by the moving mechanism, and an image processor configured to align the common regions between the plurality of first images, generate a plurality of corrected images in which corrections have been made to reduce noise for the common regions based on the common regions, which have been aligned, between the plurality of first images, and generate a difference long image based on an image obtained by splicing the plurality of corrected images and an image obtained by splicing the plurality of second images or generate a difference long image by splicing images obtained by subtracting the plurality of corrected images from the plurality of second images.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

An embodiment of the present invention is hereinafter described with reference to the drawings.

This Embodiment

The configuration of an X-ray imaging apparatus 100 according to the embodiment of the present invention is now described with reference to FIGS. 1 to 3. The X-ray imaging apparatus 100 is an example of a "radiographic imaging apparatus" in the claims.
(Configuration of X-ray Imaging Apparatus)

Figure 1A:
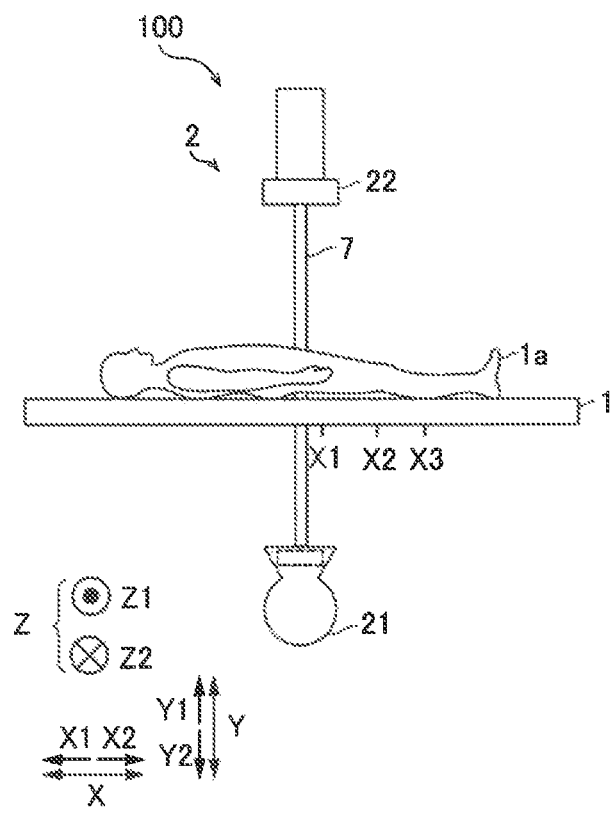
FIG. 1A is a front view showing the overall configuration of an X-ray imaging apparatus.
Figure 1B:
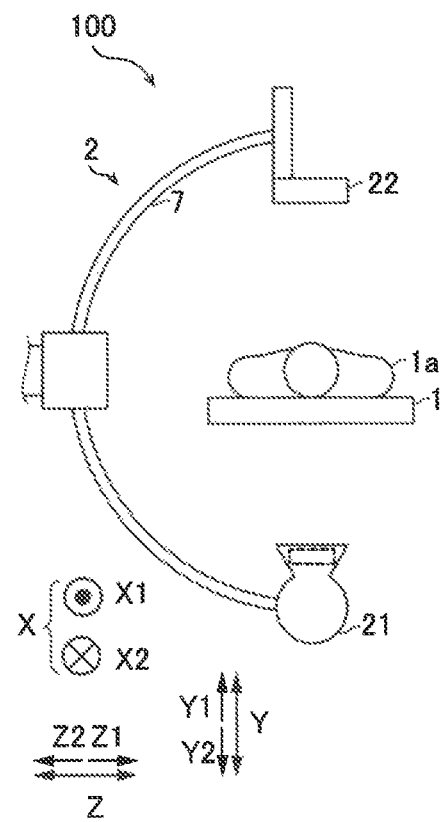
FIG. 1B is a side view showing the overall configuration of the X-ray imaging apparatus.
Figure 2:
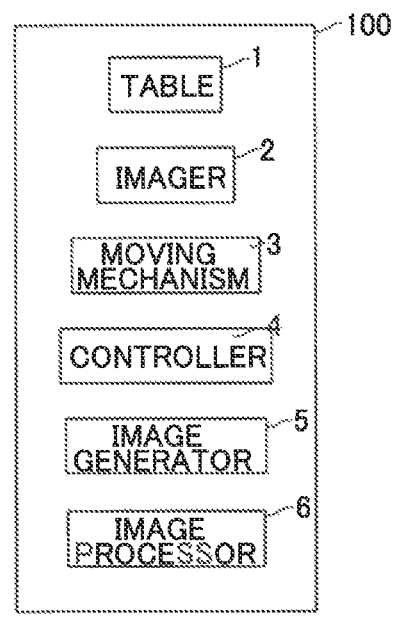
FIG. 2 is a block diagram showing the configuration of the X-ray imaging apparatus.

As shown in FIGS. 1A, 1B, and 2, the X-ray imaging apparatus 100 according to this embodiment includes a table 1, an imager 2 including an X-ray source 21 and an X-ray detector 22, a moving mechanism 3, a controller 4, an image generator 5, and an image processor 6.

A subject 1a is placed on the table 1. The table 1 has a rectangular flat plate shape in a plan view. The subject 1a is placed on the table 1 in such a manner that the head-foot direction of the subject 1a is along the long side of the rectangular shape, and the left-right direction of the subject 1a is along the short side of the rectangular shape. In this specification, the head-foot direction of the subject 1a is taken as an X direction, the left-right direction of the subject 1a is taken as a Z direction, and a direction orthogonal to the X direction and the Z direction is taken as a Y direction.

The X-ray source 21 is disposed on one side of the table 1 in the Y direction. The X-ray source 21 can radiate X-rays when a voltage is applied thereto by an X-ray tube drive (not shown). The X-ray source 21 includes a collimator capable of adjusting an X-ray field, which is an X-ray irradiation range. In this embodiment, the X-ray source 21 is attached to the tip of a C-shaped arm 7 on one side (Y2 direction side), as shown in FIG. 1B.

The X-ray detector 22 is attached to the tip of the arm 7 on the other side (the side opposite to the X-ray source 21). That is, the X-ray detector 22 is disposed on the other side (the side opposite to the X-ray source 21) of the table 1 in the Y direction with the table 1 interposed between the X-ray detector 22 and the X-ray source 21. The X-ray detector 22 is configured to detect X-rays. The X-ray detector 22 is a flat panel detector (FPD), for example. In the present embodiment, the X-ray detector 22 is attached to the Y1 direction side of the arm 7.

The X-ray source 21 is configured to irradiate the subject 1a with X-rays in a state in which the subject 1a is placed on the table 1. The X-ray detector 22 is configured to detect the X-rays transmitted through the subject 1a and output detection signals.

As shown in FIG. 2, the moving mechanism 3 is configured to move one or both of the table 1 and the imager 2 in any one of the X direction, the Y direction, and the Z direction (see FIG. 1A). The relative position between the table 1 and the imager 2 is changed such that a position (imaging position) at which the subject 1a is imaged can be changed. In this embodiment, the moving mechanism 3 is configured to move only the table 1.

The controller 4 is a computer including a central processing unit (CPU), a read-only memory (ROM), and a random access memory (RAM).

The controller 4 is configured or programmed to acquire position information of the table 1 moved by the moving mechanism 3. A plurality of position coordinates (X, Y, Z) are used as the position information of the table 1. The controller 4 is configured or programmed to control the image generator 5 to generate X-ray images including mask images 10 (see FIG. 3A) and live images 20 (see FIG. 3B) in association with the relative position coordinates of the table 1. The relative position coordinate of the table 1 at the imaging position is a coordinate associated with an X-ray image. Although X-rays are radially radiated from the X-ray source 21 such that a plurality of relative position coordinates may be included, a relative position coordinate at which the optical axis of the X-ray source 21 intersects with the table 1 is associated with the X-ray image. The mask images 10 are examples of a "first image" in the claims. The live image 20 is an example of a "second image" in the claims.

The image generator 5 is configured to generate the mask images 10 and the live image 20 based on the X-ray detection signals output from the X-ray detector 22. The mask images 10 are images captured without administering a contrast agent to the subject 1a. The live image 20 is an image captured with administering the contrast agent to the subject 1a in order to image a blood vessel 1b. The image generator 5 is configured to generate the mask images 10 when the subject 1a is imaged in a state in which no contrast agent is administered to the subject 1a. The image generator 5 is configured to generate the live image 20 when the subject 1a is imaged in a state in which the contrast agent is administered to the subject 1a.

Figure 3A:
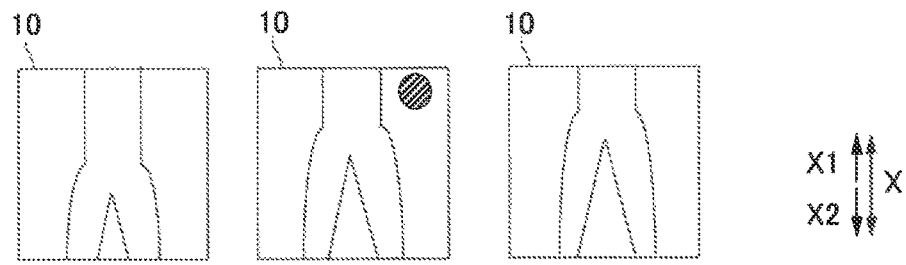
FIG. 3A is a diagram for illustrating mask images.
Figure 3B:
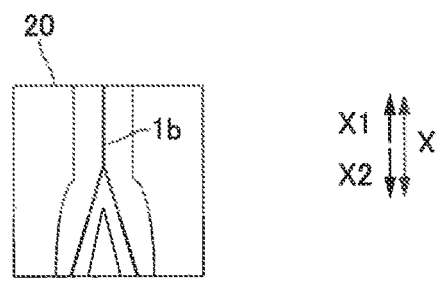
FIG. 3B is a diagram for illustrating a live image.

FIGS. 3A and 3B show the mask images 10 and the live image 20 obtained when the blood vessel 1b of the lower limb is imaged. As shown in FIG. 3A, there is no significant difference in the attenuation of transmitted X-rays between the blood vessel 1b and the surrounding tissue, and thus the blood vessel 1b of the subject 1a is not clearly captured in the mask images 10 (FIG. 3A shows images in which the blood vessel 1b is not captured). As shown in FIG. 3B, in the live image 20 captured by administering the contrast agent and increasing the attenuation of the transmitted X-rays, the blood vessel 1b of the subject 1a is clearly captured.

As shown in FIG. 2, the image processor 6 is a computer including a processor such as a graphics processing unit (GPU) or a field-programmable gate array (FPGA) configured for image processing. The image processor 6 functions as an image processing apparatus by executing an image processing program.
(Generation of Difference Long Image)

Generation of a difference long image 50 (see FIG. 9) according to this embodiment is now described with reference to FIGS. 4 to 9. In this embodiment, the X-ray imaging apparatus 100 is configured to capture the mask images 10 and the live image 20 while moving the table 1 in an X1 direction. The mask images 10 and the live image 20 have the same imaging conditions such as the relative position between the table 1 and the imager 2 at an imaging start position and the imaging speed of the table 1 moved by the moving mechanism 3. In this embodiment, the mask images 10 and the live image 20 are captured while the table 1 is continuously moved.

A plurality of mask images 10 and a plurality of live images 20 are captured. The captured mask images 10 and live images 20 are associated with the relative position coordinates, respectively. The imaging conditions are the same, and thus the mask images 10 and the live images 20 are images captured at the same relative position coordinates Xn.

The image generator 5 is configured to generate the live images 20 captured by administering the contrast agent to the subject 1a. Furthermore, the image generator 5 is configured to generate the mask images 10 captured without administering the contrast agent to the subject 1a. The order of imaging is not particularly limited.

Figure 4:
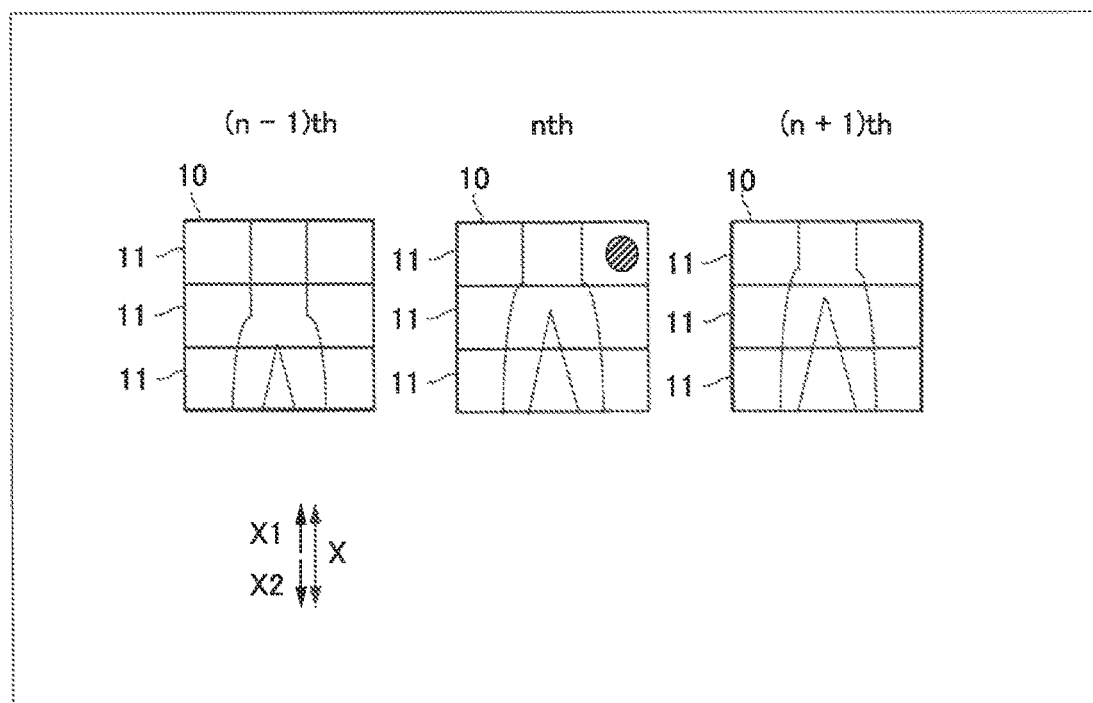
FIG. 4 is a diagram for illustrating the mask images containing a plurality of imaging regions.

As shown in FIG. 4, the imager 2 of the X-ray imaging apparatus 100 according to this embodiment is configured to image the subject 1a in such a manner that each of the mask images 10 includes a plurality of imaging regions 11 obtained by dividing the subject 1a, and includes an imaging region 11 common to at least one of the imaging regions 11 of the adjacent mask image 10. The imaging regions 11 are portions used to generate the difference long image 50. In this embodiment, the imaging regions 11 located at the centers of the mask images 10 and the live images 20 are used when the difference long image 50 is generated.

An example in which a corrected image 30 is created from the mask image 10 in which the imaging position is associated with the relative position coordinate X2 of the table 1 is now described with reference to FIGS. 4 to 9. It is assumed that the imaging region 11 is located at the relative position coordinate X2 of the table 1. Furthermore, it is assumed that noise 8 appears in a portion of the mask image 10 corresponding to the imaging region 11.

As shown in FIG. 4, the controller 4 is configured or programmed to perform control of acquiring the relative position coordinate of the table 1 associated with an nth mask image 10 to be corrected from the mask image 10. Specifically, an imaging region 11 located at the center of the mask image 10 (the optical axis of the X-ray source 21 and its surroundings) is corrected. The controller 4 is configured or programmed to perform control of specifying common regions between images from a predetermined number of mask images 10.

When using a predetermined number m of mask images 10 in addition to the nth mask image 10 to be corrected, the controller 4 sets the number of mask images 10 captured before the nth mask image 10 to m/2 and sets the number of mask images 10 captured after the nth mask image 10 to m/2. When m is an odd number, one of the number of mask images 10 captured before the nth mask image 10 and the number of mask images 10 captured after the nth mask image 10 is one more than the other. For example, when the predetermined number is two, the controller 4 performs control of specifying common regions from an (n−1)th mask image 10 captured before immediately before the nth mask image 10 and an (n+1)th mask image 10 captured after the nth mask image 10. The case in which the imaging region 11 of the nth mask image 10 is corrected using the (n−1)th mask image 10 and the (n+1)th mask image 10 is described below.

The controller 4 specifies common regions between the plurality of mask images 10 based on the relative position coordinates of the table 1 and the pixel sizes of the mask images 10.

Figure 5A:
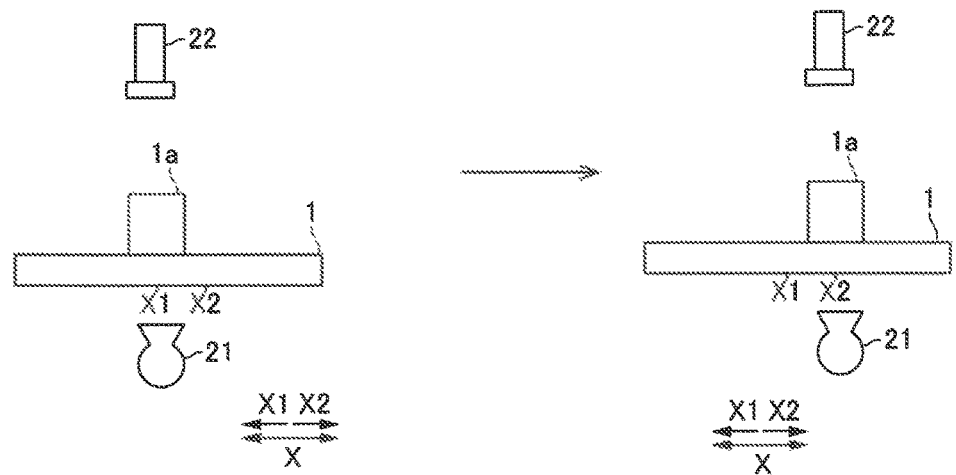
FIG. 5A is a diagram showing the relationship between movement of a table and pixels and a diagram showing movement of the table.
Figure 5B:
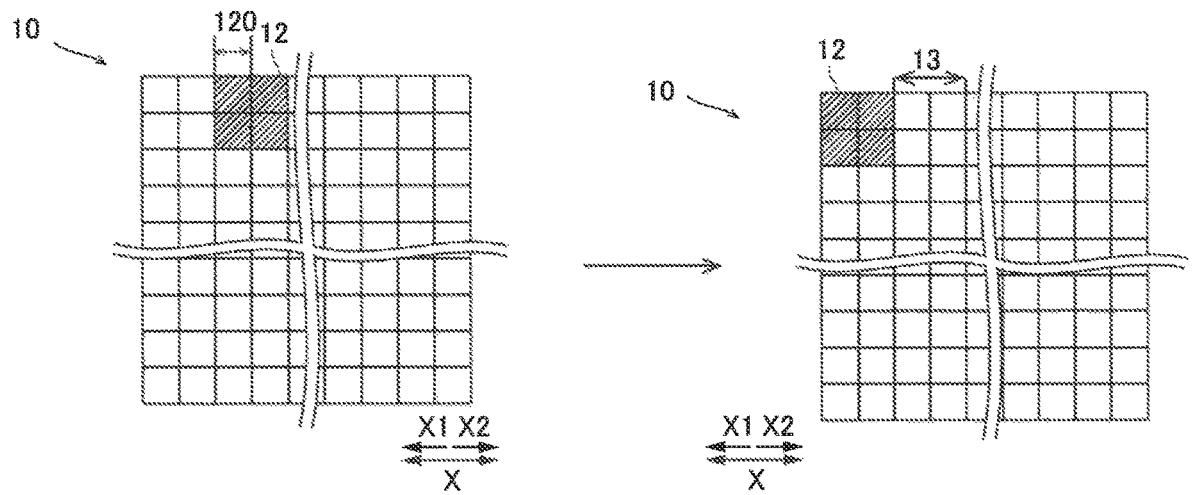
FIG. 5B is a diagram showing the relationship between movement of the table and the pixels and a diagram showing movement of the shadow of a subject accompanying the movement of the table in FIG. 5A.

The relationship between the relative position coordinate of the table 1 and the pixel size of the mask image 10 is now described with reference to FIGS. 5A and 5B. FIG. 5A shows a state in which the subject 1a is placed on the table 1 and is imaged at the relative position coordinate X1 of the table 1, and then the table 1 is moved from the relative position coordinate X1 to X2 and the subject 1a is imaged. In FIG. 5A, the subject 1a is represented by a square for convenience. The C-shaped arm 7 is omitted. FIG. 5B simply shows a pixel 12 of the X-ray detector 22. FIG. 5B represents one mask image 10 as a whole, and a small square represents one pixel of the mask image 10. The pixel size refers to the length of one side 120 of one pixel.

As shown in FIG. 5A, for example, when the table 1 is moved from the relative position coordinate X1 to the relative position coordinate X2 and the subject 1a is imaged, the shadow (indicated by hatching) of the subject 1a moves as shown in FIG. 5B. In this case, the shadow of the subject 1a has moved by two pixels, and thus the movement amount 13 of the subject 1a in the mask image 10 accompanying one coordinate movement of the table 1 is two pixels long.

Thus, the controller 4 is configured or programmed to calculate the movement amount 13 of the subject 1a in the mask image 10 with respect to movement of the table 1 from the relationship between the relative position coordinate of the table 1 and the pixel size of the pixel 12 of the mask image 10.

FIGS. 5A and 5B are used to briefly describe a method for acquiring the movement amount 13, but the size of the subject 1a in the mask image 10 changes depending on the relative position (relative distance) between the table 1, the X-ray source 21, and the X-ray detector 22 and the irradiation angle of the X-ray source 21, and thus the movement amount 13 cannot be accurately acquired. Therefore, the relative position (relative distance) between the X-ray source 21, the X-ray detector 22, and the table 1 is fixed from the start to the end of capturing the mask image 10.

In this embodiment, the moving mechanism 3 is configured to move the table 1 at a constant speed in order to make the movement amount 13 in the mask image 10 constant.

The controller 4 specifies common regions between the plurality of mask images 10 from the acquired movement amount 13.

The table 1 is configured to move in the X1 direction. As shown in FIG. 4, the common imaging region 11 moves in the X1 direction by the movement amount 13 between the (n−1)th mask image 10 and the nth mask image 10. Therefore, the controller 4 is configured or programmed to specify a region of the pixel 12 moved by the movement amount 13 in an X2 direction from a region of the pixel 12 of the imaging region 11 in the nth image, and specify a region of the pixel 12 of the corresponding (n−1)th mask image 10 as a common region.

The common imaging region 11 moves in the X1 direction by the movement amount 13 between the nth mask image 10 and the (n+1)th mask image 10. Therefore, the controller 4 is configured or programmed to specify a region of the pixel 12 moved by the movement amount 13 in the X1 direction from the region of the pixel 12 of the imaging region 11 in the nth image, and specify a region of the pixel 12 of the corresponding (n+1)th mask image 10 as a common region.

Figure 6:
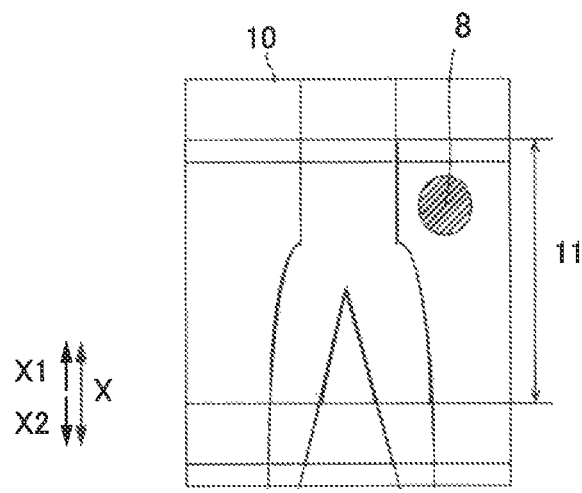
FIG. 6 is a diagram showing the superimposed mask images.

As shown in FIG. 6, the controller 4 is configured or programmed to control the image processor 6 to superimpose the common regions by moving the (n−1)th mask image 10 in the X1 direction by the movement amount 13 and moving the (n+1)th mask image 10 in the X2 direction by the movement amount 13 to superimpose the (n−1)th mask image 10 and the (n+1)th mask image 10 on the nth mask image 10 when specifying common regions between the (n+1)th mask image 10, the nth mask image 10, and the (n−1)th mask image 10. In FIG. 6, all the imaging regions 11 are illustrated, but the image processor 6 is configured to perform processing of extracting and superimposing only the common regions (imaging regions 11).

Figure 7:
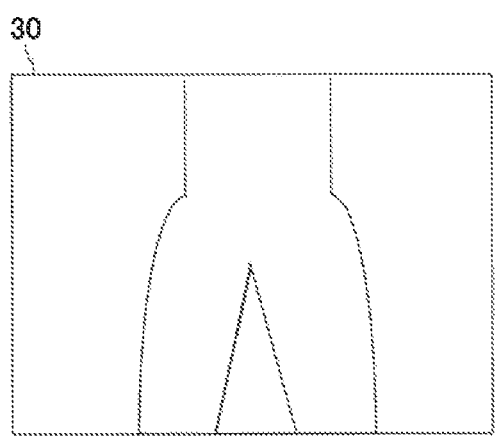
FIG. 7 is a diagram showing a corrected image.

The image processor 6 is configured to make a correction to reduce the noise 8 by averaging the different pixels 12 between the common regions of the mask images 10. When the averaging is performed, there is no change in the pixel values of the pixels 12 in common portions between the mask images 10, and the corrected image 30 in which a non-common portion (noise 8) has been reduced is generated. For example, when three mask images 10 are averaged (the pixel values are made substantially the same between the three mask images), the pixel values of the common portions are added such that the pixel value substantially three times the pixel value of one image is obtained, and even if it is averaged, the original value is only obtained. On the other hand, even if the three mask images 10 are added, the same value as the original pixel value is obtained, and thus the noise 8 that appears in only one image is reduced to one third on average. In FIG. 7, the noise 8 is deleted to show that the noise has been reduced.

The image processor 6 corrects the mask images 10 used to generate the difference long image 50 and generates the corrected image 30. The image processor 6 is configured to generate the corrected image 30 for each imaging region 11 used when the difference long image 50 is generated.

Figure 9:
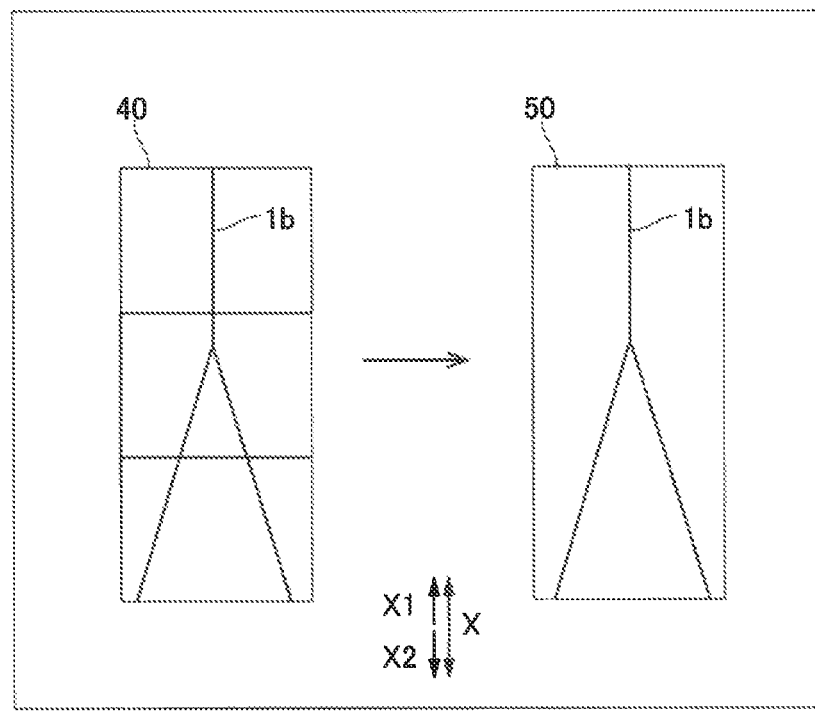
FIG. 9 is a diagram showing a difference long image.

As shown in FIG. 9, the image processor 6 extracts the imaging region 11 that has been corrected. The image processor 6 extracts the imaging region 11 of the live image 20 having the same relative position coordinate of the table 1 as that of the imaging region 11 that has been corrected, and performs subtraction processing between the imaging region 11 of the corrected image 30 and the extracted imaging region 11 of the live image 20 to generate a digital subtraction angiography (DSA) image 40 in which only the blood vessel 1b has been extracted.

The DSA image 40 is an image in which the blood vessel 1b to be imaged has been clarified. The image processor 6 is configured to generate the DSA image 40 by subtracting the mask image 10 (the blood vessel 1b is not clear) obtained by imaging portions other than the blood vessel 1b or the corrected image 30 from the live image 20 obtained by imaging the blood vessel 1b and the tissues such as bones other than the blood vessel 1b. The image processor 6 is configured to generate the DSA image 40 for each relative position coordinate of the table 1.

Figure 8:
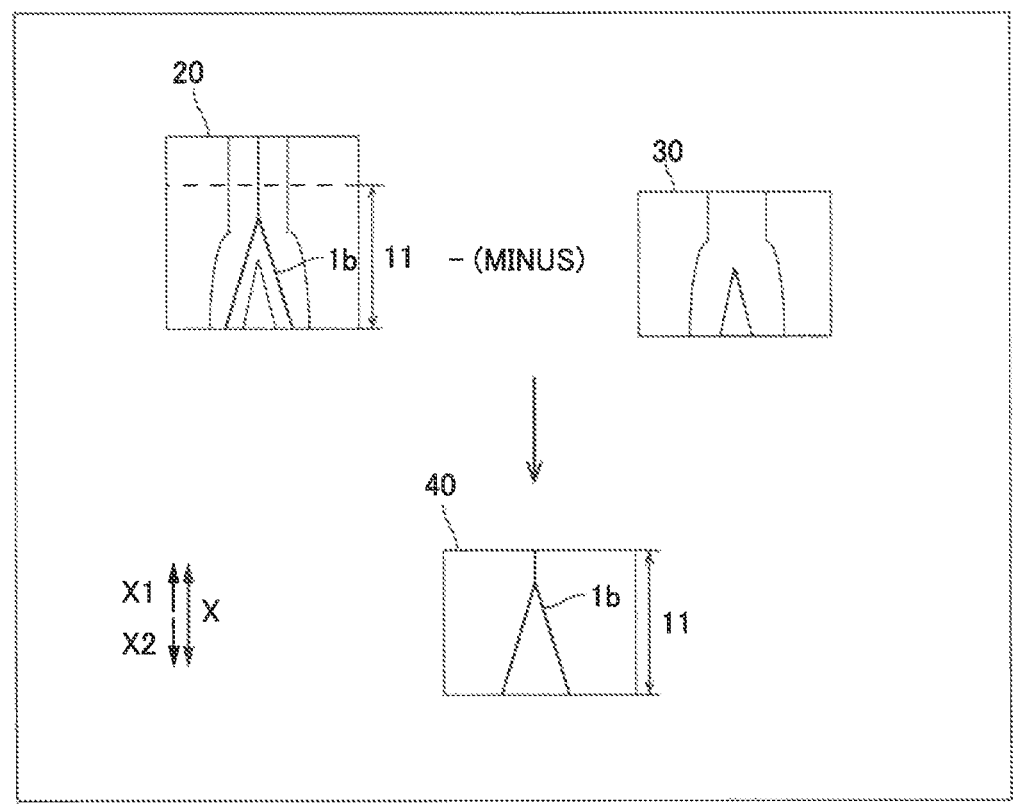
FIG. 8 is a diagram showing a DSA image.

As shown in FIG. 8, the image processor 6 generates the difference long image 50 by splicing the DSA images 40. The image processor 6 is configured to generate the difference long image 50 by splicing the DSA images 40 in the order of the relative position coordinate of the table 1 based on the relative position coordinate of the table 1.

(Artifact Removal)

In this embodiment, X-ray images are captured while the relative position between the imager 2 and the table 1 is changed from the lower abdomen toward the toes. Therefore, the position of the subject 1a changes due to movement of the subject 1a during capturing of the X-ray images, and artifacts are generated. Furthermore, the position of the subject 1a changes due to movement of the subject 1a after capturing of the live images 20 and before capturing of the mask images 30, and artifacts are generated. The artifacts (motion artifacts) are generated such that the visibility of the blood vessel 1b deteriorates. Here, it is assumed that the artifacts are generated due to movement of the subject 1a, and the noise 8 is generated not when the subject 1a is moved but when the images are generated.

The image processor 6 is configured to correct a positional deviation between the position of the subject 1a in the live images 20 and the position of the subject 1a in the mask images 10 for each pixel 12 (move the pixels 12 of the mask images 10) when generating the DSA images 40. At this time, the image processor 6 is configured to correct the positional deviation for each pixel 12 (move the pixels 12 in the mask images 10) based on the pixel values in the live images 20 and the pixel values in the mask images 10.

The positional deviation of the subject 1a between the live images 20 and the mask images 10 is corrected for each pixel 12 such that even when the subject 1a non-linearly moves before and after administration of the contrast agent, the artifacts generated in the DSA images 40 can be significantly reduced or prevented.

Figure 10:
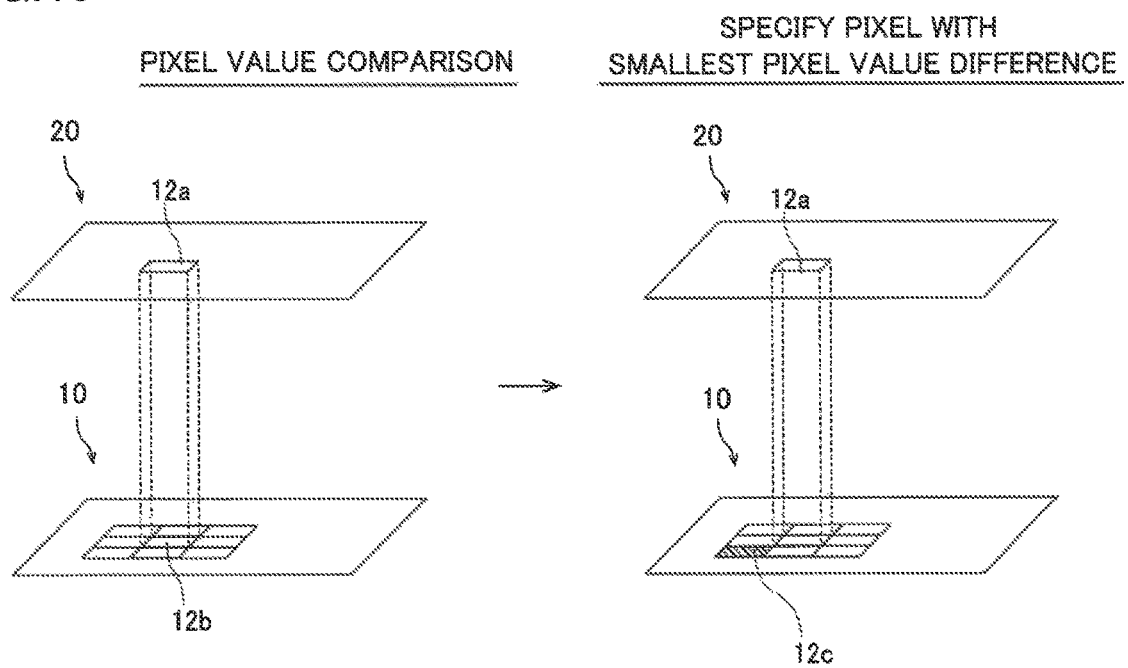
FIG. 10 is a diagram for illustrating a comparison of a pixel of the live image with a pixel of a mask image corresponding to the pixel of the live image.
Figure 11:
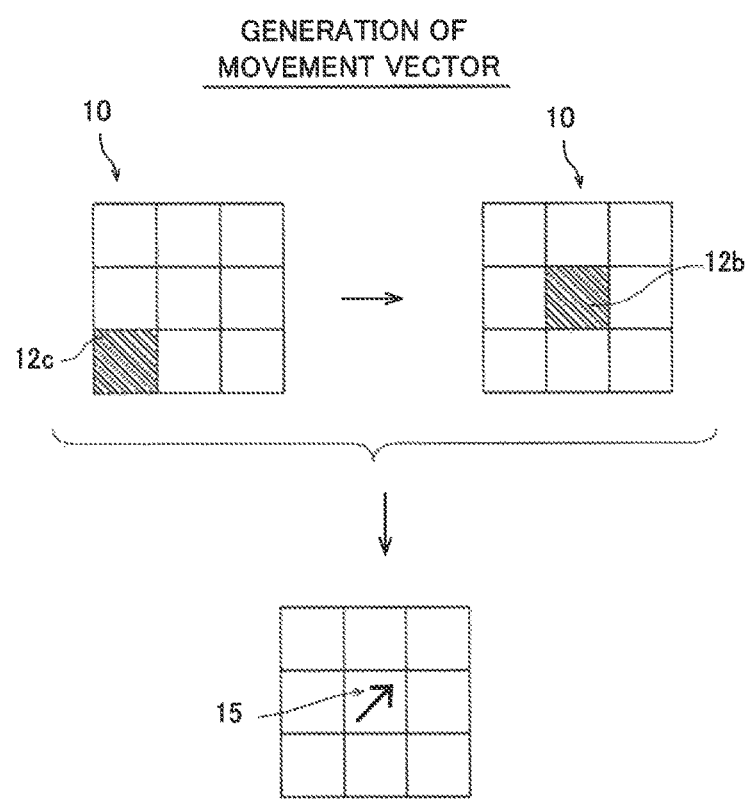
FIG. 11 is a diagram for illustrating generation of a movement vector.

As shown in FIGS. 10 and 11, the controller 4 is configured or programmed to perform control of generating a movement vector 15 representing the moving direction and the movement amount of the pixel 12 of the mask image 10 based on the pixel value of a pixel 12a of the live image 20 and the pixel value of the mask image 10. As the pixel value of the mask image 10, a pixel value having the smallest difference from the pixel value of the pixel 12 of the live image 20 is used.

The controller 4 is configured or programmed to perform control of comparing the pixel value of a certain pixel 12a of the live image 20 with the pixel value of a pixel 12b of the mask image 10 corresponding to the pixel 12a (having the same coordinate). Furthermore, the controller 4 is configured or programmed to perform control of comparing the pixel values of a total of nine pixels 12 including the corresponding pixel 12b and pixels 12 in a predetermined region around the corresponding pixel 12b (a total of eight pixels 12 including upper, upper right, right, lower right, lower, lower left, left, and upper left pixels with respect to the corresponding pixel 12b) with the pixel value of the pixel 12a of the live image 20. Furthermore, the controller 4 is configured or programmed to perform control of specifying a pixel 12 having the smallest difference in pixel value from the pixel 12a of the live image 20 from the nine pixels 12 of the mask image 10.

The controller 4 is configured or programmed to perform control of acquiring the positional deviations of the pixels 12 of the mask image 10 with respect to the pixel 12a of the live image 20 by comparing the pixel 12a of the live image 20 with the nine pixels 12 of the mask image 10 including the pixel at the same coordinate as that of the pixel 12a and the surrounding pixels 12. The controller 4 is configured or programmed to perform control of setting the pixel 12c of the mask image 10 having the smallest difference in pixel value to a pixel 12 that is most likely to be positionally deviated from a position corresponding to the pixel 12a of the live image 20. Furthermore, as shown in FIG. 11, the controller 4 is configured or programmed to perform control of acquiring the moving direction and the movement amount of the pixel 12c having the smallest difference in pixel value in the case in which the pixel 12c having the smallest difference in pixel value is moved to the position of the pixel 12b of the mask image 10 corresponding to the pixel 12a of the live image 20 (at the same coordinate) as the movement vector 15 corresponding to the pixel 12b of the mask image 10.

Figure 12:
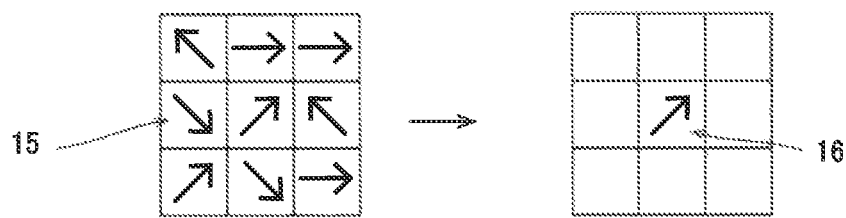
FIG. 12 is a diagram for illustrating generation of a smoothed movement vector.

As shown in FIG. 12, the controller 4 calculates a smoothed movement vector 16 obtained by smoothing the movement vector 15 associated with each pixel 12 in the mask image 10 with the pixel 12 and the surrounding eight pixels 12. Note that the smoothing can be performed by simply averaging the movement vectors 15 with the nine pixels 12, for example. Thus, even when excessively different movement vectors 15 are included in the nine pixels 12, the movement vectors 15 are averaged such that the influence of the excessively different movement vectors 15 is reduced.

The controller 4 is configured or programmed to perform control of associating the generated smoothed movement vector 16 with the pixel 12c of the mask image 10 corresponding to the pixel 12a of the live image 20. The controller 4 performs this association control on all the pixels 12 of the mask image 10 such that the smoothed movement vector 16 is associated with all the pixels 12 of the mask image 10.

The controller 4 is configured or programmed to perform control of generating an image in which the pixel 12 of the mask image 10 is moved based on the smoothed movement vector 16.

Specifically, the controller 4 is configured or programmed to perform control of moving the pixel 12 of the mask image 10 based on the smoothed movement vector 16. That is, the controller 4 performs control of moving a certain pixel 12 in the mask image 10 by the moving direction and the movement amount 13 of the smoothed movement vector 16 associated with the pixel 12 in the mask image 10. The movement of the pixel 12 based on the smoothed movement vector 16 is performed for each pixel 12 of the mask image 10 on the entire mask image 10 such that the mask image 10 becomes a mask image 10 subjected to the positional deviation correction.

Figure 13:
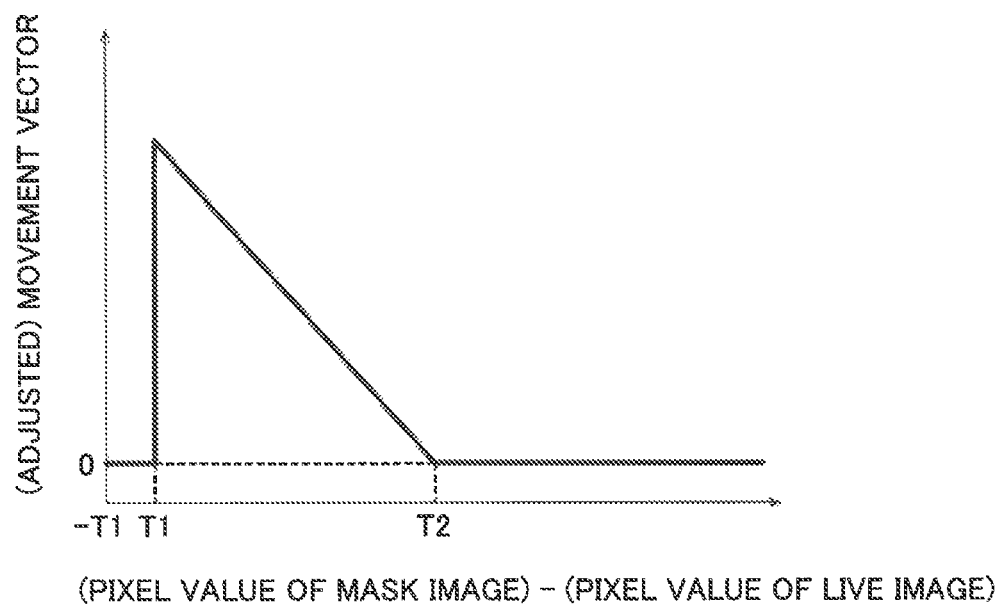
FIG. 13 is a diagram for illustrating adjustment of the movement amount (movement vector) of the pixel of the mask image.

As shown in FIG. 13, the controller 4 is configured or programmed to perform control of setting the movement amount 13 (the magnitude of the movement vector 15) of the pixel 12 of the mask image 10 to 0 when a difference between the pixel value of the pixel 12 of the live image 20 and the pixel value of the pixel 12 of the mask image 10 corresponding to the pixel 12 of the live image 20 is equal to or less than a first threshold T1. That is, the controller 4 considers that there is almost no positional deviation between the pixel 12 of the live image 20 and the pixel 12 of the mask image 10 corresponding to the pixel 12 of the live image 20, and does not perform control of moving the pixel 12 of the mask image 10 when the difference between the pixel value of the pixel 12 of the live image 20 and the pixel value of the pixel 12 of the mask image 10 corresponding to the pixel 12 of the live image 20 is equal to or less than the first threshold T1 set in advance.

The controller 4 is configured or programmed to gradually increase the moving amount 13 of the pixel 12 of the mask image 10 as the pixel value difference decreases when the difference between the pixel value of the pixel 12 of the live image 20 and the pixel value of the pixel 12 of the mask image 10 corresponding to the pixel 12 of the live image 20 is less than a second threshold T2. The second threshold T2 is larger than the first threshold T1.

Artifacts are generated due to movement of the subject 1a during capturing of the plurality of mask images 10. Also in this case, the same processing as the artifact removal performed between the mask image 10 and the live image 20 is performed.

The controller 4 is configured or programmed to perform control of removing the artifacts between the mask images 10. The controller 4 is configured or programmed to perform control of removing the artifacts of the imaging regions 11 for correcting the mask images 10 after alignment of the imaging regions and before generation of the corrected image 30. The artifact removal is the same as above. The controller 4 is configured or programmed to control the imager processor 6 to generate the corrected image 30 using the mask images 10 from which the artifacts have been removed.

Advantages of this Embodiment

According to this embodiment, the following advantages are obtained.

According to this embodiment, the X-ray imaging apparatus 100 includes the image generator 5 configured to generate the plurality of mask images 10 obtained by imaging the subject 1a in such a manner as to include the common regions between the images while the relative position between the table 1 and the imager 2 is changed, and the plurality of live images 20 obtained by imaging the subject 1a while the relative position between the table 1 and the imager 2 is changed, and the image processor 6 configured to generate the difference long image 50 by aligning the common regions between the plurality of mask images 10, generating the corrected images 30 in which corrections have been made to reduce the noise 8 for the common regions based on the aligned common regions between the plurality of images, and splicing the images obtained by subtracting the plurality of corrected images 30 from the plurality of live images 20. Accordingly, the image processor 6 can generate the corrected images 30 based on the mask images 30 captured while the imaging position is changed by aligning the common regions between the plurality of mask images 10 and making a correction to reduce the noise 8 for the common regions based on the aligned common regions between the plurality of images. Therefore, the corrected images 30 can be generated from the mask images 10 generated based on one imaging of the subject 1a. Moreover, the subject 1a is not imaged a plurality of times, and thus the amount of radiation exposure to the subject 1a can be significantly reduced. In addition, the plurality of images are aligned, and the corrected images 30 are generated such that the noise 8 can be reduced similarly to the case in which X-ray image capturing for generating the difference long image 50 and X-ray image capturing for correction are performed separately. Consequently, a decrease in the quality of the difference long image 50 can be significantly reduced or prevented while an increase in the amount of radiation exposure to the subject 1a is significantly reduced or prevented.

According to this embodiment, the mask image 10 is an image captured without administering the contrast agent to the subject 1a, and the live image 20 is an image captured with administering the contrast agent to the subject 1a. Accordingly, the subtraction processing is performed between the imaging region 11 of the mask image 10 and the imaging region 11 of the live image 20 such that the DSA image 40 in which only the blood vessel 1b has been extracted can be generated.

According to this embodiment, the X-ray imaging apparatus 100 further includes the controller 4 configured or programmed to perform control of specifying the common regions between the plurality of mask images 10 based on the relative position coordinates of the table 1 or the imager 2 and the pixel sizes of the mask images 10. Accordingly, the controller 4 performs control of specifying the common regions based on the relative position coordinate, and thus the image processor 6 can reliably align the mask images 10.

According to this embodiment, the image processor 6 is configured to generate the corrected images 30 by averaging different pixel values of corresponding pixels 12 in the common regions, which have been aligned, between the plurality of mask images 10. Accordingly, the mask images 10 are averaged such that the pixel value of the noise 8 that appears at random in the pixels of the mask image 10 can be averaged with the number of mask images 10 without changing the pixel values of the subject 1a that appear in common in corresponding pixels between the mask images 10, and thus the pixel value of the noise 8 is reduced by the number of mask images 10 used to average the pixel value. Therefore, the noise 8 can be reduced.

According to this embodiment, the imager 2 is configured to image the subject 1a in such a manner that each of the mask images 10 includes the plurality of imaging regions 11 obtained by dividing the subject 1a and at least one of the imaging regions 11 of one of the mask images 10 adjacent to each other and at least one of the imaging regions 11 of the other of the mask images 10 adjacent to each other are the common regions, and the image processor 6 is configured to align the mask images 10 using the entirety of at least one of the imaging regions 11 of each of the plurality of mask images 10 as the common region, and generate the corrected image 30 for each of the imaging regions 11. Accordingly, at least one of the imaging regions 11 is common between the adjacent mask images 10 (with consecutive imaging timings), and thus the image processor 6 can easily align the mask images 10 by using the adjacent mask images 10 and can generate the corrected image 30.

According to this embodiment, the imager 2 is configured to start to capture the mask image 10 and the live image 20 at the same relative position. Accordingly, the X-ray imaging apparatus 100 can use the imaging conditions used when the mask image 10 is captured to capture the live image 20. Consequently, a user does not need to set the imaging conditions again.

According to this embodiment, the imager 2 is configured to capture the mask image 10 and the live image 20 at the same imaging speed and the same imaging position. Accordingly, the X-ray imaging apparatus 100 captures the mask image 10 under the same imaging conditions as those of the live image 20, and thus it becomes easier to align the mask image 10 (corrected image 30) and the live image 20 in order to generate the difference long image 50.

Modified Examples

The embodiment disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

For example, while the radiographic imaging apparatus is an X-ray imaging apparatus in the aforementioned embodiment, the present invention is not limited to this. In the present invention, the radiographic imaging apparatus may alternatively be an imaging apparatus using radiation that does not affect the subject, such as gamma rays.

While a correction is made based on the relative position coordinate of the table and the pixel size in the aforementioned embodiment, the present invention is not limited to this. In the present invention, common regions may alternatively be extracted from mask images captured at different imaging positions by image recognition, and alignment may alternatively be performed such that the extracted regions overlap each other. In this case, the relative position coordinate of the table and the pixel size are not necessary.

While the moving mechanism moves the table in the aforementioned embodiment, the present invention is not limited to this. In the present invention, the moving mechanism may alternatively move the imager, or may alternatively move both the table and the imager.

While the mask image includes three imaging regions in the aforementioned embodiment, the present invention is not limited to this. In the present invention, the only requirement is that there be common regions between the mask images, and thus the number of imaging regions included in the mask image may alternatively be two or four or more.

While the moving mechanism 3 is configured to move the table at the constant speed in the aforementioned embodiment, the present invention is not limited to this. In the present invention, the user may alternatively move the table, and when the table is moved by the user, the controller may alternatively perform control of correcting the position based on the relative position coordinate.

While the predetermined number of mask images used for the corrected image is two in the aforementioned embodiment, the present invention is not limited to this. In the present invention, the predetermined number may alternatively be three or more.

While the image processor is configured to generate the long image after generating the DSA image in the aforementioned embodiment, the present invention is not limited to this. In the present invention, the image processor may alternatively be configured to generate the DSA image by subtracting the long image of the mask image from the long image of the live image.

While the X-ray imaging apparatus removes the artifacts in the aforementioned embodiment, the present invention is not limited to this. In the present invention, when there is no movement of the subject, the X-ray imaging apparatus may not remove the artifacts.

Aspects

It will be appreciated by those skilled in the art that the exemplary embodiments described above are specific examples of the following aspects.

(Item 1)

A radiographic imaging apparatus comprising:

a table on which a subject is placed;

an imager configured to irradiate the subject placed on the table with radiation and detect the radiation transmitted through the subject to image the subject;

a moving mechanism configured to change a relative position between the table and the imager;

an image generator configured to generate a plurality of first images (mask images) obtained by imaging the subject in such a manner as to include common regions between the plurality of first images while the relative position between the table and the imager is changed by the moving mechanism, and a plurality of second images (live images) obtained by imaging the subject while the relative position between the table and the imager is changed by the moving mechanism; and an image processor configured to align the common regions between the plurality of first images, generate a plurality of corrected images in which corrections have been made to reduce noise for the common regions based on the common regions, which have been aligned, between the plurality of first images, and generate a difference long image based on an image obtained by splicing the plurality of corrected images and an image obtained by splicing the plurality of second images or generate a difference long image by splicing images obtained by subtracting the plurality of corrected images from the plurality of second images.

(Item 2)

The radiographic imaging apparatus according to item 1, wherein the plurality of first images are images captured without administering a contrast agent to the subject; and the plurality of second images are images captured with administering the contrast agent to the subject.

(Item 3)

The radiographic imaging apparatus according to item 1 or 2, further comprising a controller configured or programmed to perform control of specifying the common regions between the plurality of first images based on relative position coordinates of the table or the imager and pixel sizes of the plurality of first images.

(Item 4)

The radiographic imaging apparatus according to any one of items 1 to 3, wherein the image processor is configured to generate the plurality of corrected images by averaging different pixel values of corresponding pixels in the common regions, which have been aligned, between the plurality of first images.

(Item 5)

The radiographic imaging apparatus according to any one of items 1 to 4, wherein the imager is configured to image the subject in such a manner that each of the plurality of first images includes a plurality of imaging regions obtained by dividing the subject and at least one of the plurality of imaging regions of one of the first images adjacent to each other and at least one of the plurality of imaging regions of the other of the first images adjacent to each other are the common regions; and the image processor is configured to align the plurality of first images using an entirety of at least one of the plurality of imaging regions of each of the plurality of first images as a common region, and generate a corrected image for each of the plurality of imaging regions.

(Item 6)

The radiographic imaging apparatus according to any one of items 1 to 5, wherein the imager is configured to start to capture the plurality of first images and the plurality of second images at a same relative position.

(Item 7)

The radiographic imaging apparatus according to any one of items 1 to 6, wherein the imager is configured to capture the plurality of first images and the plurality of second images at a same imaging speed and at a same imaging position.

What is claimed is:

1. A radiographic imaging apparatus comprising:
a table on which a subject is placed;
an imager configured to irradiate the subject placed on the table with radiation and detect the radiation transmitted through the subject to image the subject;
a moving mechanism configured to change a relative position between the table and the imager;
an image generator configured to generate a plurality of first images obtained by imaging the subject in such a manner as to include common regions between the plurality of first images while the relative position between the table and the imager is changed by the moving mechanism, and a plurality of second images obtained by imaging the subject while the relative position between the table and the imager is changed by the moving mechanism; and
an image processor configured to generate a plurality of corrected images consisting of the common regions in which corrections have been made to reduce noise for the common regions based on the common regions, and generate a difference long image based on an image obtained by splicing the plurality of corrected images in an adjacent state and an image obtained by splicing the plurality of second images or generate a difference long image based on an image by splicing images obtained by subtracting the plurality of corrected images from the plurality of second images.

2. The radiographic imaging apparatus according to claim 1, wherein the plurality of first images are images captured without administering a contrast agent to the subject; and the plurality of second images are images captured with administering the contrast agent to the subject.

3. The radiographic imaging apparatus according to claim 1, further comprising a controller configured or programmed to perform control of specifying the common regions between the plurality of first images based on relative position coordinates of the table or the imager and pixel sizes of the plurality of first images.

4. The radiographic imaging apparatus according to claim 1, wherein the imager is configured to start to capture the plurality of first images and the plurality of second images at a same relative position.

5. The radiographic imaging apparatus according to claim 1, wherein the imager is configured to capture the plurality of first images and the plurality of second images at a same imaging speed and at a same imaging position.

6. The radiographic imaging apparatus according to claim 1, wherein the image processor is configured to align the common regions between the plurality of first images.

7. The radiographic imaging apparatus according to claim 6, wherein the image processor is configured to generate the plurality of corrected images by averaging different pixel values of corresponding pixels in the common regions, which have been aligned, between the plurality of first images.

8. The radiographic imaging apparatus according to claim 6, wherein:

the imager is configured to image the subject in such a manner that each of the plurality of first images includes a plurality of imaging regions obtained by dividing the subject and at least one of the plurality of imaging regions of one of the first images adjacent to each other and at least one of the plurality of imaging regions of the other of the first images adjacent to each other are the common regions; and the image processor is configured to align the plurality of first images using an entirety of at least one of the plurality of imaging regions of each of the plurality of first images as a common region, and generate a corrected image for each of the plurality of imaging regions.

* * * * *